United States Patent [19]

Nelson

[11] 4,316,888

[45] Feb. 23, 1982

[54] METHOD AND COMPOSITION OF REDUCING PAIN

[75] Inventor: Eric L. Nelson, Santa Ana, Calif.

[73] Assignee: Nelson Research & Development Co., Irvine, Calif.

[21] Appl. No.: 140,493

[22] Filed: Apr. 15, 1980

[51] Int. Cl.³ .................. A61K 33/00; A61K 33/10; A61K 33/08; A61K 31/485

[52] U.S. Cl. .................. 424/127; 424/156; 424/157; 424/184; 424/260

[58] Field of Search .............. 424/157, 260, 127, 184, 424/156, 155, 244

[56] References Cited

U.S. PATENT DOCUMENTS

| | | | |
|---|---|---|---|
| 2,934,472 | 4/1960 | May | 424/184 |
| 3,108,041 | 10/1963 | Weiner | 424/260 |
| 3,140,978 | 7/1964 | Zentner | 424/260 |
| 3,427,379 | 2/1969 | Barry et al. | 424/260 |
| 3,767,794 | 10/1973 | McVean et al. | 424/184 |
| 3,919,237 | 11/1973 | Halder | 424/260 |

OTHER PUBLICATIONS

*Chemical Abstracts,* vol. 82, 1975, 93155k.
*The Merck Index,* Ninth Ed. (1976), Merck & Co. Rahway, N.J., article 7908.
*The Merck Index,* Ninth Ed., Merck & Co. Inc., Rahway, N.J. 1976, pp. 990, 1112, 48 and App-1.
*Handbook of Nonprescription Drugs,* pub. by American Pharm. Assoc., Wash., D.C. 1977, pp. 84, 89, 91, 94, 97-100, 109, 102-104, 106, 108.
*Life Sciences,* vol. 15, pp. 1665-1672, No. 9.

*Primary Examiner*—Frederick E. Waddell
*Attorney, Agent, or Firm*—Martin A. Voet

[57] ABSTRACT

A method for temporarily reducing pain in animals including humans, and especially pain associated with gastrointestinal dysfunction, by administering to an animal having pain an effective, pain reducing amount of dextromethorphan, preferably as the hydrobromide.

10 Claims, No Drawings

METHOD AND COMPOSITION OF REDUCING PAIN

BACKGROUND OF THE INVENTION

1. Field of the Invention

The invention relates to a method of treatment for pain. More particularly the invention relates to a method for temporarily reducing pain in humans associated with gastrointestinal dysfunctions such as peptic ulcer.

2. Background of the Prior Art

A peptic ulcer is a circumscribed discontinuity in the surface of the gastrointestinal mucosa which occurs in areas bathed by acid-pepin. Peptic ulcers are classified according to location, that is, gastric, duodenal, esophageal or marginal.

The major symptom of chronic duodenal ulcer disease is pain in the epigastrium. The "testbook" periodic pain syndrome of nonradiating epigastric pain, characterized by onset one to three hours after eating, relief by food, antacids, or vomiting, absence before breakfast, but frequently awakening the patient at night and occurring in clusters of daily pain for a few weeks followed by longer pain free intervals, is actually present in at least 50 percent of duodenal ulcer patients. Many patients have varied descriptions of the character of the pain, for example, discomfort, heartburn, cramping, burning and gnawing.

Cause of ulcer pain is unknown. There are numerous, poorly controlled studies that report pain relief with mechanical or chemical removal of acid and some controlled studies that cast doubt on the pain-relieving qualities of antacids.

Endoscopic observation fails to correlate subjective "degree of pain" with size or depth of ulcer.

SUMMARY OF THE INVENTION

Dextromethorphan is an old compound used heretofore as an antitussive. It is marketed in a wide variety of "over-the-counter" (OTC) and prescription (Rx) products for relief of cough, typically as the hydrobromide. It is described in the art consistently as having no known analgesic activity.

Notwithstanding the long established belief that dextromethorphan has no analgesic activity, it has now been discovered that dextromethorphan is useful in the temporary reduction of pain and especially pain associated with gastrointestinal dysfunction.

More particularly, the invention relates to a method of temporarily reducing pain in animals comprising administering to an animal having pain an effective, pain reducing amount of dextromethorphan.

The invention also relates to a method for temporarily reducing pain associated with gastrointestinal dysfunction in humans comprising administering to a human having pain associated with gastrointestinal dysfunction, an effective, pain reducing amount of dextromethorphan hydrobromide.

The invention further relates to pharmaceutical compositions comprising an effective, pain reducing amount of dextromethorphan and preferably dextromethorphan hydrobromide in combination with one or more of the following:

(1) An effective, gastric acid secretion inhibiting amount of a histamine $H_2$ receptor antagonist, such as cimetidine; or (2) An effective acid neutralizing amount of an antacid; or (3) An effective acid neutralizing amount of an anticholinergic drug, such as atropine, belladonna, homatropine, methscopolamine bromide and scopolamine hydrobromide, or (4) An effective gas reducing amount of an antiflatulent, such as simethicone.

DETAILED DESCRIPTION OF THE INVENTION

Dextromethorphan (d-3-methoxy-N-methylmorphinan) is the d-isomer of the codeine analog of levophornal; however, unlike the l isomer, it has consistently been reported by the prior art as having no analgesic properties. The compound is well known in the art as a cough suppressant (antitussive) and is commercially available; e.g., U.S. Pat. No. 2,676,177 and Höfliger. et al, Helv. Chim. Acta 39, 2053 (1956). The hydrobromide salt of dextromethorphan is widely commercially used as an "over-the-counter" (OTC) orally administered antitussive. It is also used as an antitussive in combination with antihistamines in prescription (Rx) products for cold remedies.

Dextromethorphan may be used in the present invention in daily dosage amounts between about 1 mg and 1,000 mg and preferably between about 10 mg and about 500 mg depending on the age and weight of the animal to be treated and the type of pain to be treated. A typical daily dosage amount suitable for a human varies between about 1 mg and about 200 mg and preferably between about 10 mg and 100 mg. For example, a typical dosage amount of dextromethorphan hydrobromide effective in temporarily reducing pain associated with gastrointestinal dysfunction in an adult human male would be about 10 mg to about 50 mg administered in equal doses 1 to 4 times per day.

Antacids which may be used in combination with dextromethorphan in the present invention are conventional antacids which are well known and widely used in the treatment of a variety of excess acid related gastrointestinal dysfunctions including acid indigestion, heartburn, sour stomach and ulcers. Typical antacids include, for example, sodium bicarbonate, calcium carbonate, magnesium hydroxide and aluminum hydroxide. Antacids may be used in the present invention in combination with dextromethorphan in dosage amounts conventionally used for treatment of a variety of excess acid related gastrointestinal dysfunctions, as discussed above.

Anticholinergic drugs which may be used in combination with dextromethorphan in the present invention include those anticholinergics conventionally used in the treatment of peptic ulcers. Typical anticholinergic drugs used for this purpose include, for example, atropine, belladonna, homatropine, methscopolamine bromide and scopolamine hydrobromide. Anticholinergic drugs may be used in the present invention in combination with dextromethorphan in dosage amounts conventionally used in the treatment of peptic ulcers.

Histamine $H_2$ receptor antagonists which may be used in combination with dextromethorphan in the present invention include those histamine $H_2$ receptor antagonists which are conventionally used in the treatment of peptic ulcers, such as, for example, cimetidine and other histamine $H_2$ receptor antagonists including ranitidine and tiquinamide. Histamine $H_2$ receptor antagonists may be used in the present invention with dextromethorphan in dosage amounts conventionally used in the treatment of peptic ulcers.

Antiflatulents which may be used in combination with dextromethorphan in the present invention include those antiflatulents which are conventionally used in the treatment of gastrointestinal dysfuntion, such as, for example, simethicone. Antiflatulents may be used in the present invention with dextromethorphan in dosage amounts conventionally used in the treatment of gastrointestinal dysfunction.

For therapeutic use, dextromethorphan will normally be administered as a pharmaceutical composition in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and preferably hydrobromic.

Other pharmacologically active compounds may, in certain cases, be included in the composition. Advantageously, the composition will be made up in a dosage unit form appropriate to the desired mode of administration, for example, as a tablet, capsule, oral suspension, injectable solution or as a cream for topical administration.

The pharmaceutical compositions may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with nontoxic pharmaceutically acceptable excipients which are suitable for manufacture of tablets. These excipients may be, inert diluents, for example calcium carbonate, sodium carbonate, lactose, calcium phosphate or sodium phosphate; granulating and disintegrating agents, for example, maize starch, or alginic acid; binding agents, for example, starch, gelatine or acacia, and lubricating agents, for example, magnesium stearate or stearic acid. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with an oil medium, for example, arachis oil, liquid paraffin or olive oil.

Aqueous suspensions contain the active ingredients in admixture with excipients suitable for the manufacture of aqueous suspensions. Such excipients are suspending agents, for example, sodium carboxymethyl cellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, for example, polyoxyethylene sorbitol monnoleate, or condensation product of ethylene oxide with partial esters derived from fatty acids and hexitol anhydrides, for example, polyoxyethylene sorbitan monooleate. The said aqueous suspensions may also contain one or more preservatives, for example, ethyl, or n-propyl, p-hydroxy benzoate, one or more coloring agents, one or more flavoring agents and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a nontoxic parenterally-acceptable diluent or solvent, for example, as a solution in 1,3-butane diol.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form will generally contain between about 100 mg and about 500 mg of the active ingredient of the formula stated above.

From the foregoing formulation discussion, it is apparent that the composition of this invention can be administered topically, orally or parenterally. The term parenteral as used herein includes subcutaneous injection, intravenous, intramuscular, or intrasternal injection or infusion techniques.

The scientific basis of the discovery set forth herein is not fully understood; however, it is believed that dextromethorphan is able to exert its pain reducing activity by acting upon specific pain mediating receptors in the body, and particularly in the gastrointestinal area, associated with endogenous peptides recently discovered to be involved in the mediation of pain in animals including humans, which peptides are known as enkephalins.

The term "animals" as used herein refers generally to animals including humans. The phrase "pain associated with gastrointestinal dysfunction" as used herein refers to pain associated with a wide variety of gastrointestinal ailments and conditions including diseases or conditions, such as, for example, acid indigestion, heartburn, sour stomach, gas associated with the foregoing conditions and peptic ulcer disease of the esophagus, stomach and duodenum; a large and varied category of dyspepsia of unknown origin including cancer of the stomach, infiltrative disease of the stomach including lymphoma; Crohn's disease, eosinophilic granuloma, tuberculosis, syphilis and sarcoidosis, abdominal lesions, chronic pancreatis, bilary disease, colic, Zollinger-Ellison syndrome, and other diseases and conditions of the gastrointestinal tract.

The following examples are shown for the purpose of illustration only and should not be deemed as limiting the scope of the invention.

EXAMPLE I

Patient, human male with diagnosis of duodenal ulcer, was awakened at 1:30 a.m. with gastric pain. Twenty mg dextromethorphan hydrobromide powder was dissolved in 100 cc of water and administered to the patient orally. Patient reported pain was relieved within 5 minutes and patient returned to sleep. Patient was again awakened with gastric pain at 4:05 a.m. Ten mg dextromethorphan hydrobromide powder was dissolved in 50 cc of water and administered orally. Patient reported pain was relieved within 10 minutes and patient returned to sleep. Patient again awakened at 6:00 a.m. with gastric pain. Twenty mg dextromethorphan hydrobromide powder was dissolved in 100 cc of water and administered to the patient orally. Patient reported pain was relieved in 5 minutes.

EXAMPLE II

Patient, human male with diagnosis of duodenal ulcer, was awakened with thoracic pain at 1:00 p.m. Patient orally administered two commercially available conventional antacid tablets, which did not relieve the pain. At 2:30 a.m., pain was reported as being more severe and two additional antacid tablets were taken with no pain relief. Discomfort continued until 4:00 a.m. when patient orally administered 20 mg of dextromethorphan hydrobromide in a conventional syrup. Pain was reported as being relieved within 15 minutes.

I claim:

1. A method of temporarily reducing pain associated with gastrointestinal dysfunction in humans comprising administering to a human having pain associated with gastrointestinal dysfunction an effective, pain reducing amount of dextromethorphan or a pharmaceutically acceptable salt thereof.

2. The method of claim 1 wherein the dextromethorphan is administered in a daily dosage regimen of about 1 mg to about 200 mg.

3. The method of claim 1 wherein the dextromethorphan is administered in a daily dosage regimen of about 10 mg to about 100 mg.

4. The method of claim 1 wherein the dextromethorphan is administered in the form of its hydrobromide salt.

5. The method of claim 4 wherein the dextromethorphan hydrobromide is administered orally.

6. The method of claim 1 wherein the dextromethorphan is administered in an oral dosage form selected from the group consisting of a tablet, capsule, lozenge, syrup, suspension and elixir.

7. The method of claim 6 wherein the oral dosage form additionally comprises an effective, gastric acid neutralizing amount of an antacid.

8. The method of claim 6 wherein the oral dosage form additionally comprises an effective gas inhibiting amount of an antiflatulent.

9. The method of claim 8 wherein the antiflatulent is simethicone.

10. The method of claim 6 wherein the oral dosage form additionally comprises an effective, gastric acid neutralizing amount of an antacid and an effective, gas inhibiting amount of an antiflatulent.

* * * * *